(12) United States Patent
Yaroshenko et al.

(10) Patent No.: US 11,116,470 B2
(45) Date of Patent: Sep. 14, 2021

(54) BEAM HARDENING CORRECTION IN X-RAY DARK-FIELD IMAGING

(71) Applicant: KONINKLIJKE PHILIPS N.V., Eindhoven (NL)

(72) Inventors: Andriy Yaroshenko, Garching (DE); Hanns-Ingo Maack, Norderstedt (DE); Thomas Koehler, Norderstedt (NL); Fabio De Marco, Eindhoven (NL); Lukas Benedict Gromann, Freising (DE); Willer Konstantin, Eindhoven (NL); Peter Noel, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 44 days.

(21) Appl. No.: 16/606,418

(22) PCT Filed: Apr. 17, 2018

(86) PCT No.: PCT/EP2018/059745
§ 371 (c)(1),
(2) Date: Oct. 18, 2019

(87) PCT Pub. No.: WO2018/192909
PCT Pub. Date: Oct. 25, 2018

(65) Prior Publication Data
US 2020/0187893 A1 Jun. 18, 2020

(30) Foreign Application Priority Data

Apr. 20, 2017 (EP) .................................. 17167384

(51) Int. Cl.
*A61B 6/00* (2006.01)
*G01T 7/00* (2006.01)

(52) U.S. Cl.
CPC ............ *A61B 6/583* (2013.01); *A61B 6/4241* (2013.01); *A61B 6/482* (2013.01); *A61B 6/484* (2013.01); *A61B 6/5258* (2013.01); *G01T 7/005* (2013.01)

(58) Field of Classification Search
CPC ..... A61B 6/4241; A61B 6/583; A61B 6/4291; A61B 6/482; A61B 6/484; A61B 6/032; A61B 6/5205; A61B 6/5258; G06T 11/005
See application file for complete search history.

(56) References Cited

U.S. PATENT DOCUMENTS

| 2004/0101104 | A1 | 5/2004 | Avinash |
| 2012/0257810 | A1 | 10/2012 | Von Berg |
| 2016/0242726 | A1* | 8/2016 | Koehler ............... A61B 6/5258 |

FOREIGN PATENT DOCUMENTS

| WO | WO2012029039 A1 | 3/2012 |
| WO | WO2015067511 A1 | 5/2015 |
| WO | WO2016177903 A1 | 11/2016 |

OTHER PUBLICATIONS

PCT International Search Report, International application No. PCT/EP2018/059745, dated Jul. 5, 2018.

(Continued)

*Primary Examiner* — Courtney D Thomas
(74) *Attorney, Agent, or Firm* — Larry Liberchuk

(57) ABSTRACT

The invention relates to beam hardening correction in X-ray Dark-Field imaging of a subject including a first material and a second material, the first and second material having different beam hardening properties. As the X-ray imaging data includes information on the internal structure of the imaged subject, such information may be used, together with appropriate calibration data to identify the beam hardening contributions occurring in the imaged area of the subject, so (Continued)

to allow for a correction of artifacts due to beam hardening in X-ray Dark-Field imaging.

15 Claims, 3 Drawing Sheets

(56) References Cited

OTHER PUBLICATIONS

Jakubek et al: "Data Processing and Image Reconstruction Methods for Pixel Detectors", Nuclear Instruments & Methods in Physics Research. Section A: Accelerators, Spectrometers, Detectors, and Associated Equipment, Elsevier BV * North-Holland, NL, vol. 576, No. 1, May 12, 2007 (May 12, 2007), pp. 223-234, XP022072116.
Pelzer Georg et al: "A Beam Hardening and Dispersion Correction for X-Ray Dark-Field Radiography", Medical Physics, AIP, Melville, NY, US, vol. 43, No. 6, May 10, 2016 (May 10, 2016), pp. 2774-2779, XP012207575.
Chabior Michael et al: "Beam Hardening Effects in Grating-Based X-Ray Phase-Contrast Imaging", Medical Physics, AIP, Melville, NY, US, vol. 38, No. 3, Feb. 11, 2011 (Feb. 11, 2011), pp. 1189-1195, XP012145111.
Pfeiffer Franz et al., "Phase Retrieval and Differential Phase-Contrast Imaging with Low-Brilliance X-Ray Sources", Nature Physics, vol. 2, Apr. 2006, pp. 258-261.
Pfeiffer F. et al., "Hard-X-Ray Dark-Field Imaging Using a Grating Interferometer", Nature Materials, vol. 7, pp. 134-137, 2008.
Alvarez Robert et al., "Energy-Selective Reconstructions in X-Ray Computerized Tomography", Physics in Medicine and Biology, Oct. 1976, vol. 21, No. 5, pp. 733-744.

\* cited by examiner

BEAM HARDENING CORRECTION IN X-RAY DARK-FIELD IMAGING

FIELD OF THE INVENTION

The invention relates to beam hardening correction in X-ray Dark-Field imaging of a subject including a first material and a second material, the first and second material having different beam hardening properties.

BACKGROUND OF THE INVENTION

There is a paper "Data processing and image reconstruction methods for pixel detectors" by Jan Jakubek (Nuclear Instruments and Methods in Physics Research A 576 (2007) 223-234 disclosing that semiconductor single-particle-counting pixel detectors offer many advantages for radiation imaging: high detection efficiency, energy discrimination, noiseless digital integration (counting), high frame rate and virtually unlimited dynamic range. All these properties allow to achieve high quality images. Examples of transmission images and 3D tomographic reconstruction using X-rays and slow neutrons are presented demonstrating effects that can affect the quality of images. A number of obstacles can limit detector performance if not handled. The pixel detector is in fact an array of individual detectors (pixels), each of them has its own efficiency, energy calibration and also noise. The common effort is to make all these parameters uniform for all pixels. However, an ideal uniformity can be never reached. Moreover, it is often seen that the signal in one pixel affects neighboring pixels due to various reasons (charge sharing, crosstalk, etc.). All such effects have to be taken into account during data processing to avoid false data interpretation. The main intention of the above paper is to summarize techniques of data processing and image correction to eliminate residual drawbacks of pixel detectors. It is shown how to extend these methods to handle further physical effects such as hardening of the beam and edge enhancement by deflection. Besides, more advanced methods of data processing such as tomographic 3D reconstruction are discussed. All methods are demonstrated on real experiments from biology and material science performed mostly with the Medipix2 pixel device. A brief view to the future of pixel detectors and their applications also including spectroscopy and particle tracking is given too.

The paper "A beam hardening and dispersion correction for x-ray dark-field radiography" by G. Pelzer et al. (Med. Phys. 43(6), June 2016, p 2774-2779) discloses that X-ray dark-field imaging promises information on the small angle scattering properties even of large samples. However, the dark-field image is correlated with the object's attenuation and phase-shift if a polychromatic x-ray spectrum is used. A method to remove part of these correlations is proposed. The experimental setup for image acquisition was modeled in a wave-field simulation to quantify the dark-field signals originating solely from a material's attenuation and phase-shift. A calibration matrix was simulated for ICRU46 breast tissue. Using the simulated data, a dark-field image of a human mastectomy sample was corrected for the finger print of attenuation- and phase-image. Comparing the simulated, attenuation-based dark-field values to a phantom measurement, a good agreement was found. Applying the proposed method to mammographic dark-field data, a reduction of the dark-field background and anatomical noise was achieved. The contrast between microcalcifications and their surrounding background was increased. The authors show that the influence of and dispersion can be quantified by simulation and, thus, measured image data can be corrected. The simulation allows to determine the corresponding dark-field artifacts for a wide range of setup parameters, like tube-voltage and filtration. The application of the proposed method to mammographic dark-field data shows an increase in contrast compared to the original image, which might simplify a further image-based diagnosis. US 2004/0101104 A1 describes a method for obtaining data including scanning an object using a multi-energy computed tomography (MECT) system to obtain data to generate an anatomical image, and decomposing the obtained data to generate a first density image representative of bone material and a second density image representative of soft-tissue. The method further includes segmenting at least one of the first density image and the second density image, and volume rendering the second density image.

In the paper "Beam hardening effects in grating-based x-ray phase-contrast imaging" by M. Chabior (Med. Phys. 3813), March 2011, pages 1189-1195, the authors investigate how beam hardening affects the image formation in x-ray phase-contrast imaging and consecutively develop a correction algorithm based on the results of the analysis. The authors' approach utilizes a recently developed x-ray imaging technique using a grating interferometer capable of visualizing the differential phase shift of a wave front traversing an object. An analytical description of beam hardening is given, highlighting differences between attenuation and phase-contrast imaging. The authors present exemplary beam hardening artifacts for a number of well-defined samples in measurements at a compact laboratory setup using a polychromatic source. Despite the differences in image formation, the authors show that beam hardening leads to a similar reduction of image quality in phase-contrast imaging as in conventional attenuation-contrast imaging. Additionally, the authors demonstrate that for homogeneous objects, beam hardening artifacts can be corrected by a linearization technique, applicable to all kinds of phase-contrast methods using polychromatic sources. The evaluated correction algorithm is shown to yield good results for a number of simple test objects and can thus be advocated in medical imaging and nondestructive testing.

WO 2016/177903 A1 describes an apparatus and related method for processing image data supplied by a scanning phase contrast or dark-field imaging apparatus (MA). Beam hardening artifact in phase contrast and dark-field imaging can be reduced by applying a beam hardening processing operation by a beam hardening processing module (BHC) in respect of a plurality of detector readings that contribute signals to the same image pixel position or geometric ray of an imaging region of the apparatus (MA). In one embodiment, a phantom body is used to acquire calibration data on which the beam hardening processing is based.

X-ray dark-field imaging is a promising new imaging modality that can, for example, help better visualize pulmonary disorders. Thereby, X-ray Dark-Field imaging presents a possibility to quantify X-ray small-angle scattering in the object. The X-ray Dark-Field signal can be acquired using a grating interferometer. The use of a grating interferometer allows for simultaneous acquisition of the X-ray Dark-Field signal and also conventional transmission. The two images are intrinsically perfectly registered and both images can be used for diagnostic purposes. In a general case, the X-ray small-angle scattering and transmission information are two independent and often complementary tissue characteristics.

It is desirable to have the X-ray scattering and transmission information separated as far as possible during image processing, so to be able to consider the obtained transmission and Dark-Field images as having complementary information. In other words, if the contributions of scattering and transmission are not sufficiently separated and isolated, the results are less (if at all) useful for diagnostic purposes.

In grating based dark-field imaging, the measured intensity depends on the relative grating position x according to (p being the period of the grating that is stepped)

$$I(x)=TI_0(1+DV_0 \cos(2\pi x/p+\psi+\phi_0))$$

where $I_0$, $V_0$, $\phi_0$ are the so-called blank scan intensity, blank-scan visibility, and blank scan phase of the fringe pattern generated by the gratings, and the quantities T, D, $\psi$ are the objects transmission, dark-field, and refraction. These three object parameters are derived by acquiring measurements for the intensity I(x) for at least three different positions x.

A further discussion and background as to grating based phase contrast may be found, for example in "Phase retrieval and differential phase-contrast imaging with low-brilliance X-ray sources" by F. Pfeiffer et al. (Nature Physics, vol. 2, April 2006, pages 258-261.

As further discussion and background as to grating based dark-field imaging may be found, for example, in "Hard-X-ray dark-field imaging using a grating interferometer" by F. Pfeiffer et al. (Nature Materials, vol. 7, 134-137 (2008), published online 20 Jan. 2008).

Basically, the small-angle scattering of the object can be correlated directly with a tissue property only if the spectral distribution in the calibration scan and the sample (patient) scan is identical or if the attenuation properties of the object are known and can be taken into consideration during the image processing/calculation. Otherwise the X-ray Dark-Field image is to be considered as corrupted, as the information on the image does not originate only from small-angle scattering but also from beam hardening properties of the object. The same tissue may create a different small angle scatter signal depending on the x-ray spectrum. Since the spectrum is affected by beam-hardening (caused by the spectral dependency of attenuation), conventionally, one cannot correlate the tissue property with the small-angle scattering based on the dark-field signal alone and the attenuating properties of the object have to be taken into account when calculating the small-angle scattering (dark field) image.

The general reason for this is that the X-ray grating interferometer is sensitive to the X-ray spectrum. This issue can significantly complicate medical image evaluation and in the worst case may even lead to a false diagnosis.

One of the present challenges of X-ray Dark-Field chest radiography is to properly address beam-hardening contributions of the fat layer, the bones, etc.

As currently, all attenuation is attributed to a single material (i.e. soft-tissue), only the beam-hardening properties of this single material (i.e. soft tissue) are taken properly into account during image processing, by using a phantom body made of polyoxymethylene (POM), polymethylmethacrylate (PMMA) or other soft-tissue equivalent plastics, having spectral properties similar to that of soft tissue, while, however, the influence of the ribcage is not considered. In order to get rid of the beam-hardening contributions for soft tissue a calibration scan is typically performed with different thicknesses of a soft-tissue equivalent material as an equivalent absorber, for example the plastic POM. Thus, calibration measurements with equivalent absorbers can be used to correct for the attenuation properties of the soft-tissue layer (e.g. fat layer). WO 2016/177903 A1 discloses an apparatus and a related method for processing image data supplied by a scanning phase contrast or dark-field imaging apparatus. Beam hardening artifacts in phase contrast and dark-field imaging are addressed by applying a beam hardening processing operation by a beam hardening processing module in respect of a plurality of detector readings that contribute signals to the same image pixel position or geometric ray of an imaging region of the apparatus. In one embodiment of WO 2016/177903 A1, a phantom body is used to acquire calibration data on which the beam hardening processing is based.

However, bones like the ribcage have significantly different spectral attenuation properties and hence they produce an artificial x-ray dark-field signal even in a scan calibrated with different phantom/absorber thicknesses corresponding to soft tissue.

SUMMARY OF THE INVENTION

It is an object of the present invention to provide for an improvement of the correction as to the beam hardening in X-ray Dark-Field imaging.

In a first aspect of the present invention a method is presented for obtaining a beam hardening map used in beam hardening correction in X-ray Dark-Field imaging of a subject including a first material and a second material, the first and second material having different beam hardening properties, wherein the method comprises an acquisition step of acquiring X-ray imaging data of the subject, an obtainment step of obtaining information as to a contribution of the first material to the acquired X-ray imaging data, and a map provision step of providing a beam hardening map as an input for the beam hardening correction in the X-ray Dark-Field imaging using the acquired X-ray imaging data, wherein the beam hardening map is based on the obtained information.

In a second aspect of the present invention a device is presented for obtaining a beam hardening map used in beam hardening correction in X-ray Dark-Field imaging of a subject including a first material and a second material, the first and second material having different beam hardening properties, the device being arranged for receiving X-ray imaging data and comprising an obtainment unit arranged to obtain information as to a contribution of the first material to the acquired X-ray imaging data, and a map provision unit arranged to provide a beam hardening map as an input for the beam hardening correction in the X-ray Dark-Field imaging using the acquired X-ray imaging data, wherein the beam hardening map is based on the obtained information.

It was found by the inventors that the improper attribution of all attenuation to a single material leads, in cases where there are materials, like bone and soft-tissue, present with different spectral properties, to incorrect results and to artifacts.

It was further realized by the inventors that the X-ray imaging data includes information on the internal structure of the imaged subject, while such information may be used, together with appropriate calibration data to identify the beam hardening contributions occurring in the imaged area of the subject, in order to allow for a correction of artifacts due to beam hardening in X-ray Dark-Field imaging.

In a preferred embodiment, the map provision step includes an estimating step of estimating a material map of the imaged area of the subject from the acquired X-ray imaging data, the material map indicating a thickness of the first material, and a transformation step of transforming the material map into the beam hardening map based on information on the beam hardening properties of the first material.

A possibility for obtaining the information lies in the use of the content of the X-ray imaging data depicting the (portion of) the subject, as one can derive from the attenuation data, for example, by image recognition or similar processing where bones are depicted and estimate the thickness (in beam direction) of the bones.

It may be noted here that in the present context transmission data and attenuation data of the X-ray imaging data are basically the same, as it is appreciated by the skilled person.

In a preferred variant of the above embodiment, the information on the beam hardening properties includes calibration data obtained from calibration X-ray imaging data obtained from imaging a first calibration material for the first material.

While it is contemplated to use data obtained by calculation, e.g. from first principles, or simulation, the present invention also allows for use of calibration data.

In a preferred version of the above variant the method further comprises a calibration step including the obtaining of calibration X-ray imaging data by X-ray imaging the first calibration material.

It is contemplated that even a single calibration data point might be sufficient, at least in cases where with sufficient accuracy one may assume that the respective beam hardening of a material depends only on a single material parameter, e.g. in the form $D_{beamhard}(T)=T^{Xmat}$. With a material parameter being $x_{mat}$, in the most simple way, such single parameter may be sufficient to describe the curves in FIG. 1 (in a log-log plot these curves become (approximately) straight lines through the origin, with $x_{mat}$ being the slope of this curve.) However this is a very simplified approach and also better models with more degrees of freedom can be used if more calibration data point (e.g. more measurements of different thicknesses of a certain material) is used.

In a preferred implementation of the above version, the calibration step includes one or more of X-ray imaging without a sample and X-ray imaging with a sample of the first calibration material, X-ray imaging of samples of the first calibration material having different thicknesses, and X-ray imaging of combined samples of the first calibration material and a second calibration material, the second calibration material being for the second material.

One approach on carrying out such calibration step includes the acquiring of a calibration scan with no sample in the beam at all, a further calibration scan with different thicknesses of a first calibration material (or reference material) and a yet further calibration scan with different thicknesses of a second calibration material (or reference material). Alternatively, such calibration may be done in a combined scan, where portions of the field of view include no sample, different thicknesses of the first calibration material, different thicknesses of the second calibration materials, and different combinations of the first and second material. Furthermore, it is also possible to provide, rather than one scan for different thicknesses of a material, different scans of the material, each with a different thickness. Provided that the detector area is sufficiently homogeneous, the different calibrations may be performed in a single imaging (or scanning) process. The more information is obtained by the calibration in total, the more robust the overall processing will be.

In a further preferred variant of the above embodiment, the information on the beam hardening properties includes at least one parameter of a parameterization of the beam hardening properties of the first material and/or calculation data obtained from simulation calculations for a beam hardening by the first material. As discussed above, a single parameter giving the slope for a log-log-version of the curves of FIG. 1 might be used for describing the beam hardening properties. Rather assuming an approximation by a straight line, a more complex set of parameters may be provided, e.g. parameters of a polynomial function (instead of a linear function).

In a further preferred embodiment, the obtainment step includes image processing on transmission data included in the acquired X-ray imaging data for identifying at least a first region corresponding to the first material in the acquired X-ray imaging data.

From the transmission data, due to the differences in appearance of the first and second material, it is possible to identify the areas of the transmission image where the first material is shown (in case of the first material being, for example, bone, such area typically also includes the attenuation resulting from the second material, e.g. soft tissue, also being in the beam path) and the areas of the transmission image where only the second material is shown (i.e. where there is no bone material in the beam path). With the invention being employed outside the area of medical imaging, there might also be situations where the X-ray image data includes an area with only the first material, another area with only the second material and a further area in which both the first and the second material are in the respective beam path.

In a further preferred embodiment, the acquired X-ray imaging data includes X-ray imaging data obtained by imaging using a first X-ray energy and X-ray imaging data obtained by imaging using a second X-ray energy different from the first X-ray energy, wherein the obtainment step includes energy processing of the X-ray imaging data for obtaining the information.

By means of dual energy imaging (i.e. using the energy processing), the different impacts of the materials on the attenuation of the X-ray beam with different energies may be employed to obtain representations of the imaged area in which the first and second materials are separated. When performing dual energy data acquisition, one can, for each pixel, separate the amount of, for example, bone and soft tissue, that was present along the beam path, so that it is not necessary (while nevertheless possible) to specifically identify regions regarding to either material. Some discussion and background information as to dual energy imaging may be found, for example, in "Energy-selective Reconstructions in X-ray Computerized Tomography" by R. E. Alvarez and A. Macovski (Phys. Med. Biol., 1976, vol. 21, no. 5, pages 733-744). As the skilled person is sufficiently familiar with the concepts and implementations of dual energy imaging, no further discussion or explanation is needed here. In a further preferred embodiment, the first material is bone and the second material is soft tissue.

The present invention may be advantageously employed, for example, in the area of human (or animal) chest imaging, while the invention is nevertheless not limited to this and may be used also in the context of other radiographic applications (including CT applications) where soft tissue and bones are present in the beam. Furthermore, the invention is also not limited to medical application and may also be used in other areas, for example in the context of the nondestructive testing.

It may be noted here that the present invention is not limited to a consideration of just two materials, as it is contemplated to employ the invention also in situations where there might be a third material having further differing spectral properties, while there might, for example, be either included further information on the third material into the beam hardening map or be provided a further beam hardening map to be used for compensating for beam hardening by the third material, in addition to the use of the beam hardening map provided, as discussed above, for the first material. A scenario involving such three materials may be a case where, in addition to soft tissue and bone, there is also included an implant in the field of view of the X-ray image. An alternative scenario where a third material may be used is the presence of contrast agent such as iodine or gadolinium. It may be needless to say that the above extends also to further materials beyond the consideration of three differing materials.

In a further preferred implementation of variant discussed above, which includes calibration data being obtained from calibration X-ray imaging data obtained from imaging a first calibration material for the first material, the first calibration material is or includes aluminum and/or calcium, each of which is considered to have spectral properties similar to those of bones.

In a version of the preferred implementation discussed above in which the calibration step includes X-ray imaging of the second calibration material, is or includes a polyoxymethylene material POM and/or a polymethylmethacrylate material PMMA, which are considered to have spectral properties similar to those of soft tissue or adipose tissue.

In a preferred embodiment, a method is provided for obtaining an X-ray Dark-Field image of a subject including a first material and a second material, the first and second material having different beam hardening properties, the method comprising the steps of the method according to the invention and particularly as discussed above, a Dark-Field image calculation step of calculating am X-ray Dark-Field image from the acquired X-ray imaging data, and a correction step including a correction of the calculated Dark-Field image as to the first material using the beam hardening map and a correction of the calculated Dark-Field image as to the second material using attenuation information of the acquired X-ray imaging data.

In a further aspect of the present invention a software product is presented for obtaining a beam hardening map used in beam hardening correction in X-ray Dark-Field imaging of a subject including a first material and a second material, the first and second material having different beam hardening properties, the software product comprising program code means for causing a computer to carry out the steps of the method according to the present invention when the software product is run on the computer.

It shall be understood that the method of claim 1, the device of claim 13, and the computer program of claim 14 have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
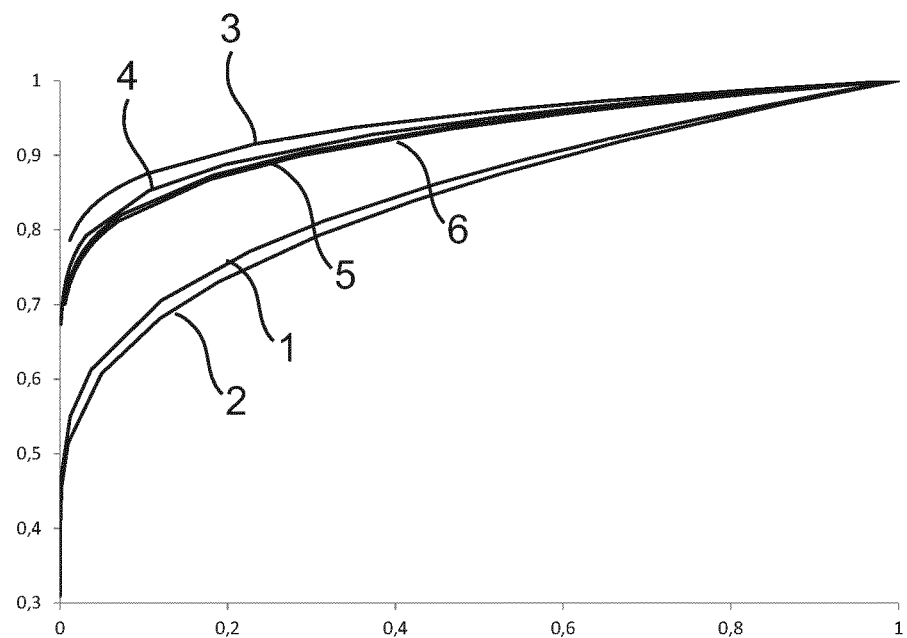
FIG. 1 shows a diagram illustrating difference between the spectral properties of bones and soft tissue and the approximation thereof by aluminum and POM.

FIG. 1 shows a diagram illustrating difference between the spectral properties of bones and soft tissue and the approximation thereof by aluminum and POM.

FIG. 1 shows results of simulated beam hardening correction for different materials. The abscissa gives the relative transmission, while the ordinate gives the relative visibility loss. The curve denoted by 1 relates to compact bone (ICRU). The curve denoted by 2 relates to aluminum. The curve denoted by 3 relates to adipose tissue. The curve denoted by 4 relates to POM. The curve denoted by 5 relates to water, while the curve denoted by 6 relates to soft tissue. These graphs have been obtained assuming a particular initial effective spectrum (given by parameters such as tube voltage, anode material, beam filtering, effective spectral response of the detector, etc.) and a particular grating interferometer (given by grating materials, heights, periods, distances). Thus, the curves show the qualitative behavior of the visibility loss as a function of transmission only for a very specific example at hand and my look different for other system parameters.

The simulated curves 1 to 6 illustrate that soft tissue andadipose tissue (and water) on the one side and bones (ICRU Bone compact) on the other side have different spectral properties and, therefore, should be accounted for using different materials in beam hardening correction. Aluminum is a good approximation for bones, whereas POM is a good substitute for the soft tissue and/or adipose tissue.

Figure 2:
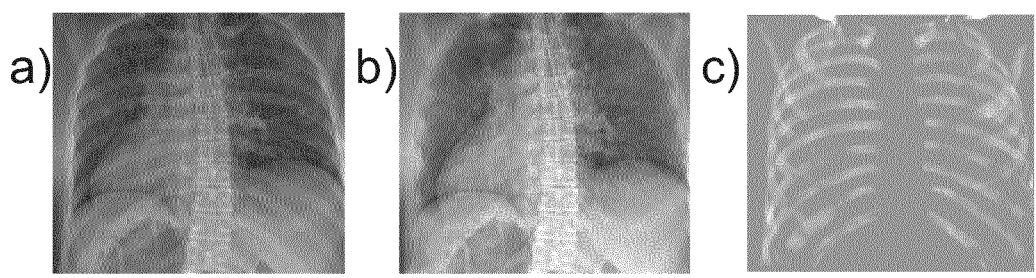
FIG. 2 shows an X-ray transmission image, together with a processed version thereof with bones removed and an indication of the bones as the difference.

FIG. 2 shows an X-ray transmission image (FIG. 2a), together with a processed version thereof (FIG. 2b)) with bones removed and an indication of the bones as the difference (FIG. 2c)).

Commercially available software, e.g. from Riverain Technologies, allows for a removal of the image portions relating to bones from X-ray images. Bone suppression in X-ray radiograms is furthermore discussed, for example, in US 2012/257810 A1.

Figure 3:
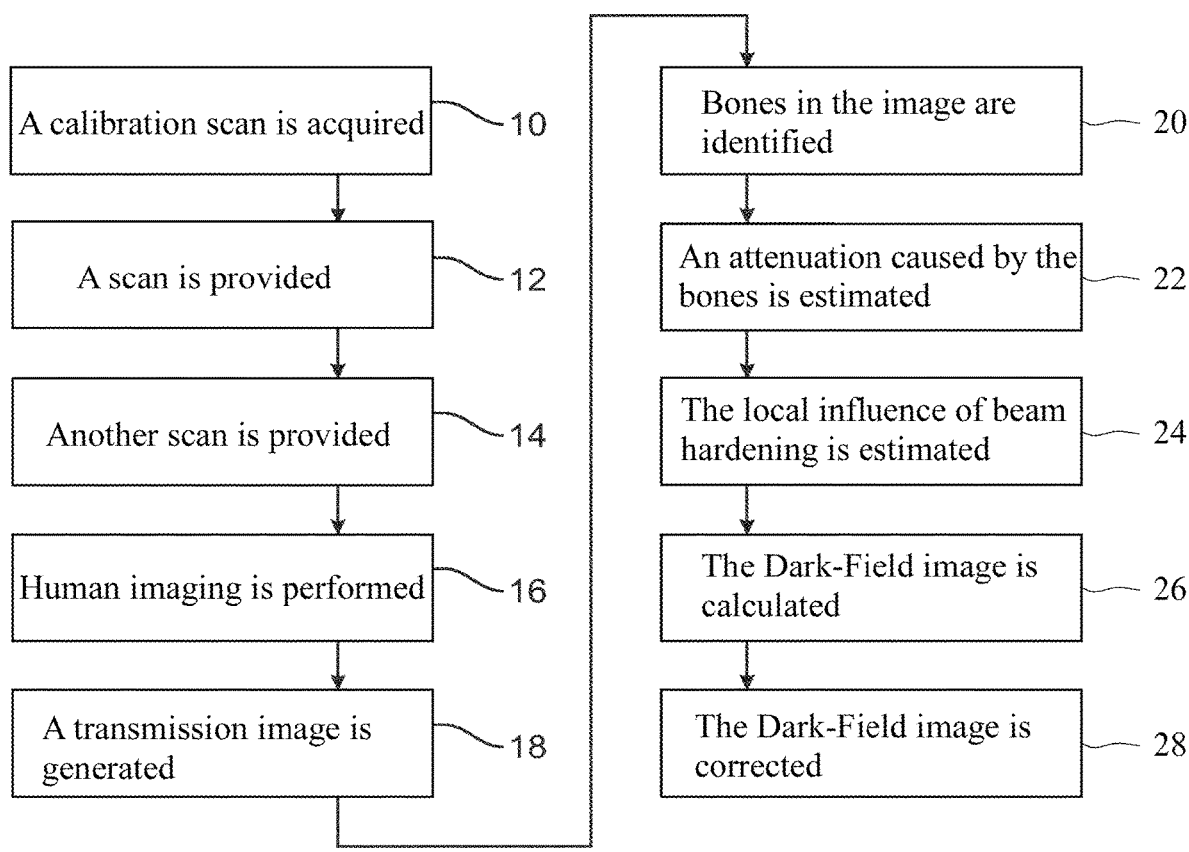
FIG. 3 shows a flow diagram illustrating a method of correcting for beam hardening according to a first embodiment of the present invention.

FIG. 3 shows a flow diagram illustrating a method of correcting for beam hardening according to a first embodiment of the present invention.

In the embodiment illustrated in FIG. 3, before human imaging is performed a calibration scan is acquired in step 10 without anything in the beam.

Further, in steps 12 and 14, two scans with different thicknesses of two different materials in the beam, respectively, are provided. The two scans are performed separately.

Here, the second calibration material has similar absorption properties to the soft tissue (e.g. plastic POM) and the first calibration material has spectral absorption properties similar to the bones (e.g. aluminum).

Subsequently, human imaging is performed (step 16) and the transmission image is generated (step 18). Based on this transmission image the bones in the image are identified (step 20) and the attenuation caused by the bones is estimated (step 22). Currently available software can generate such bitmaps with the required information.

It may be pointed out here that, conventionally, such image processing for bone identification has the purpose of generating an image without bones (as shown in FIG. 2B) where lung pathologies can be assessed more easily because the bones do not "disturb" the image. Conventionally, in such context, the bone image itself is not used but it is merely sort of waste/side product. In the context of the present invention, however, the side product (which may have only rather academic interest) is employed purposefully to a useful effect.

In step 22, the thickness of the bones is estimated.

The discussion of this exemplary embodiment is based, in the most simple case, on a model as explained in the following, while, of course, more elaborate models may be used as well:

$$T = e^{-l_{st}\mu_{st}} e^{-l_b \mu_b}$$

or equivalently, the total attenuation is given by $$-\ln T = l_{st}\mu_{st} + l_b\mu_b$$

where subscripts st and b refer to soft tissue and bone respectively, l is the length of the corresponding material along the beam and μt is the linear attenuation coefficient. The image processing (originally designed to provide a soft tissue only image $l_{st}\mu_{st}$) conducted in step 20 provides also the bone-only image ($l_b\mu_b$), see also FIG. 2c.

Subsequently, the uncorrected dark-field image is corrected for beam-hardening effects based on the estimates $l_b$ and $l_{st}$ for the lengths of the ray through bone and soft-tissue (i.e., material 1 and 2).

Specifically, in this embodiment, in step 24, the calibration information is used to estimate the local influence of beam hardening, with step 26 including the calculation of the (uncorrected) Dark-Field image, which is corrected in step 28 using the estimated thickness the bones (ribs), wherein, for the correction regarding the contribution as to the beam hardening by the soft tissue, just the attenuation value is used, as in a conventional technique. The information derived in steps 12 and 14 from a calibration in regard to the soft-tissue may be used for this.

FIG. 1 illustrates, how much the fringe visibility changes if a purely attenuation object is placed in the beam. Suppose the attenuation was caused exclusively by soft-tissue, see curve 6 in FIG. 1. Let's denote the visibility as a function of transmission by hardening correction corrects for this visibility loss and results in a dark-field value of 1 for any length of adipose tissue in the beam. Thus, the uncorrected dark-field value D is corrected by the formula $$D' = \frac{D}{V_{at}(e^{-l_{at}\mu_{at}})}$$

For the case with two materials 1 and 2, the formula $$D' = \frac{D}{V_{1,2}(e^{-l_1\mu_1}, e^{-l_2\mu_2})}$$

applies. We note that the arguments in the above formula are transmission factors, for illustrative purpose, so ease the connection to FIG. 1. Since the μ's are know, it is also possible to use just the lengths $l_1$ and $l_2$ as arguments (and integrate the exponentials in the function $V_{1,2}$).

Alternatively formulated, we can start again from $$I(x) = TI_0(1 + DV_0 \cos(2\pi x/p + \psi + \phi_0))$$

and acknowledge that the analysis of the transmission provided knowledge about the actual blank scan visibility $V_0$ for the object at hand, meaning that the model for phase retrieval is $$I(x) = TI_0(1 + DV_{1,2}(e^{-l_1\mu_1}, e^{-l_2\mu_2})\cos(2\pi x/p + \psi + \phi_0))$$

to obtain directly a dark-field image D that does not suffer from beam-hardening.

It may be noted that here $V_{1,2}$ ($e^{-l_1\mu_1}, e^{-l_2\mu_2}$) provides the beam-hardening map.

Figure 4:
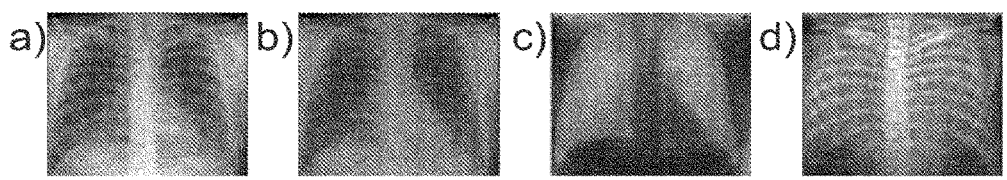
FIG. 4 shows X-ray transmission images obtained with different energies, together with processing results showing only the soft tissue and only the bones, respectively.

FIG. 4 shows X-ray transmission images obtained with different energies, together with processing results showing the only soft tissue and only the bones, respectively.

FIG. 4 a) shows a chest radiograph acquired at 56 kV as an example of a low energy image. FIG. 4 b) shows a corresponding radiograph obtained at high energy, namely 120 kV, wherein furthermore a 1 mm copper filtration is provided. In FIG. 4 c) the result of dual-energy processing as to the removal of the bone aspect is shown, with FIG. 4 d) showing the corresponding result of removal of the soft tissue.

As the skilled person is familiar with the concept of dual-energy imaging, no additional explanation thereof is necessary here.

Figure 5:
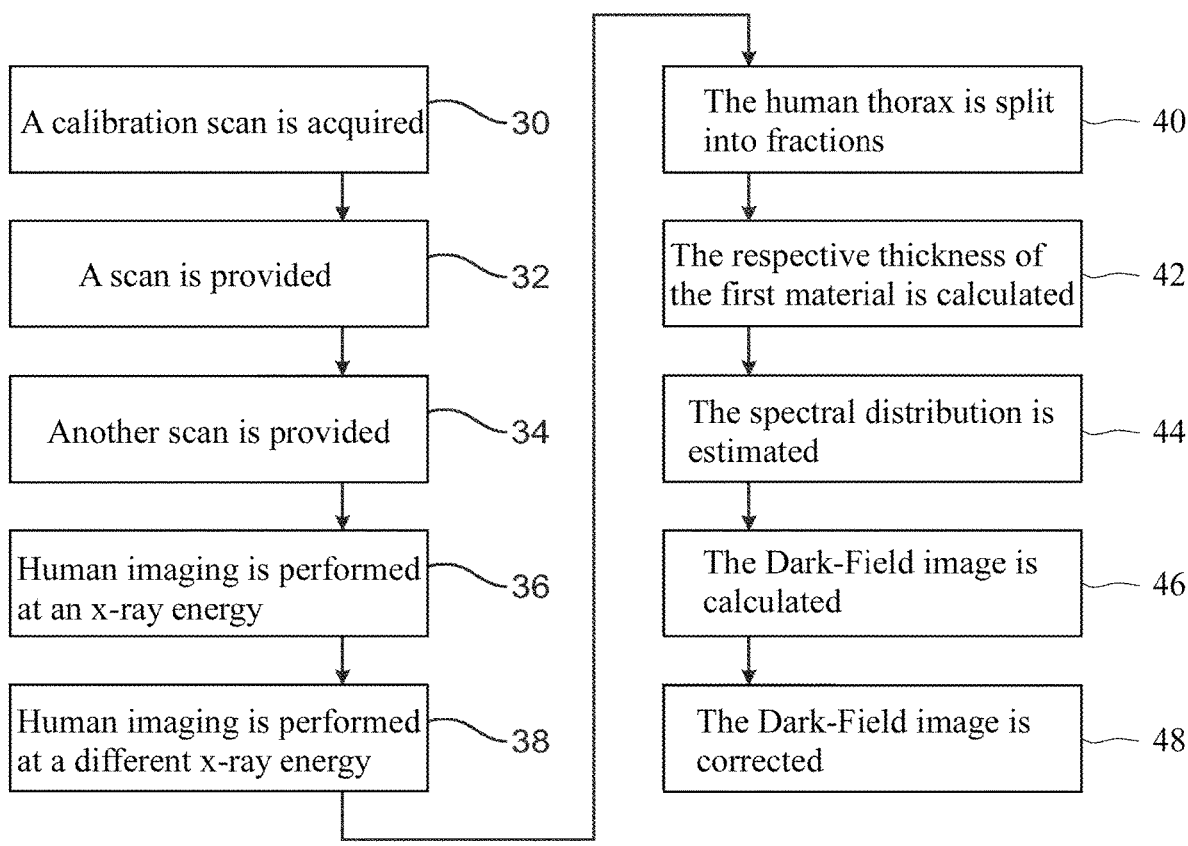
FIG. 5 shows a flow diagram illustrating a method of correcting for beam hardening according to a second embodiment of the present invention.

FIG. 5 shows a flow diagram illustrating a method of correcting for beam hardening according to a second embodiment of the present invention.

Several steps of this embodiment correspond to those discussed above as to the first embodiment.

Specifically, steps 30 to 34 including the acquisition of a blank calibration scan and calibration scans for different thicknesses of the first and second calibration materials correspond to steps 10 to 14, respectively, which are discussed above.

Deviating from the first embodiment, however, subsequently, human imaging is performed at two different x-ray energies (e.g. 56 kVp and 120 kVp) (steps 36 and 38) and the transmission images are generated (it is noted here that one of the scans may be a pure transmission scan, e.g. the 120 kVp image, and can be obtained with detuned gratings, or still tuned gratings but only one x-ray shot). Based on these transmission images, the human thorax can be split into the fraction that can be approximated by POM (e.g. soft tissue) and the fraction that is best approximated by aluminum (e.g. bones) (step 40).

Based on the "Aluminum" image information, on a pixel-by-pixel basis, the respective thickness of the first material is calculated in step 42. Thus, the bone contribution to a human thorax transmission image can be represented by a certain thickness of aluminum. This information is then used, in step 44, to estimate the spectral distribution behind the human chest. Using the calibration scans acquired with POM and aluminum, a more sophisticated beam hardening correction can be applied which will make it possible to obtain a dark field image that originates only from small-angle x-ray scattering and will have significantly less beam hardening artifacts, again, similar to the case of the first embodiment as discussed above. Indeed, steps 46 and 48 correspond to steps 26 and 28 discussed above.

Figure 6:
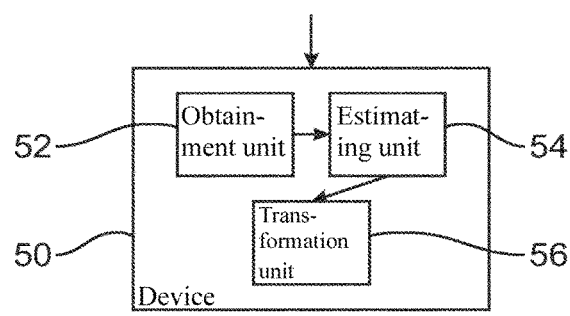
FIG. 6 shows a block diagram illustrating a device for obtaining a beam hardening map according to a further embodiment of the present invention.

FIG. 6 shows a block diagram illustrating a device for obtaining a beam hardening map according to a further embodiment of the present invention.

The device 50 is provided for obtaining a beam hardening map, which is to be used in beam hardening correction in X-ray Dark-Field imaging of a subject (with the subject including first and second materials having different beam hardening properties).

The device 50 is arranged for receiving X-ray imaging data as illustrated by the arrow arriving at the device 50.

The device 50 comprises an obtainment unit 52, an estimating unit 54 and a transformation unit 56.

The obtainment unit 52 is arranged to obtain information as to a contribution of the first material on the acquired X-ray imaging data.

The estimating unit 54 is arranged to estimate a material map of the imaged area of the subject from the acquired X-ray imaging data, so that the material map indicates a thickness of the first material in the first region.

Based on such input from the estimating unit 54, the transformation unit 56 is arranged to transform the material map into a beam hardening map, using, in the process, information on the beam hardening properties of the first material.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

It is, as such, not necessary that the calibration data is obtained before the obtaining of the imaging data, as the order may also be reversed, i.e. the calibration data may be acquired after the X-ray imaging is done on, for example, on the patient.

In the claims, the word "comprising" does not exclude other elements or steps, and the indefinite article "a" or "an" does not exclude a plurality.

A single processor, device or other unit may fulfill the functions of several items recited in the claims. The mere fact that certain measures are recited in mutually different dependent claims does not indicate that a combination of these measures cannot be used to advantage.

Operations like acquiring, identifying, estimating, transforming, obtaining, image processing, energy processing, calculating and correcting can be implemented as program code means of a computer program and/or as dedicated hardware.

A computer program may be stored and/or distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A method for obtaining a beam hardening map used in beam hardening correction in X-ray Dark-Field imaging of a subject including at least a first material and a second material, the first and second material having different beam hardening properties, the method comprising:
    acquiring X-ray imaging data of the subject;
    obtaining information as to a contribution of the first material to the acquired X-ray imaging data; and
    providing a beam hardening map as an input for the beam hardening correction in the X-ray Dark-Field imaging using the acquired X-ray imaging data, wherein the beam hardening map is based on the obtained information.

2. The method according to claim 1, further comprising:
    estimating a material map of the imaged area of the subject from the acquired X-ray imaging data, the material map indicating a thickness of the first material; and
    transforming the material map into the beam hardening map based on information on the beam hardening properties of the first material.

3. The method according to claim 1, further comprising providing image processing on transmission data included in the acquired X-ray imaging data for identifying at least a first region corresponding to the first material in the acquired X-ray imaging data.

4. The method according to claim 1, wherein the acquired X-ray imaging data includes X-ray imaging data obtained by imaging using a first X-ray energy and X-ray imaging data obtained by imaging using a second X-ray energy different from the first X-ray energy, wherein dual-energy processing of the X-ray imaging data is used for obtaining the information.

5. The method according to claim 1, wherein the first material is a bone and the second material is a soft tissue.

6. The method according to claim 1, wherein the information as to the contribution of the first material to the acquired X-ray imaging data derives from attenuation data of the acquiring X-ray imaging data.

7. The method according to claim 2, wherein the information on the beam hardening properties includes calibration data obtained from calibration X-ray imaging data obtained from imaging a first calibration material for the first material.

8. The method according to claim 2, wherein the information on the beam hardening properties includes at least one parameter of a parameterization of the beam hardening properties of the first material and/or calculation data obtained from simulation calculations for a beam hardening by the first material.

9. The method according to claim 7, further comprising:
    obtaining calibration X-ray imaging data by X-ray imaging the first calibration material.

10. The method according to claim 7, wherein the first calibration material includes at least one of aluminum and calcium.

11. The method according to claim 9, wherein calibrating comprises at least one of:
    X-ray imaging without a sample and X-ray imaging with a sample the first calibration material;
    X-ray imaging samples of the first calibration material having different thicknesses; and
    X-ray imaging combined samples of the first calibration material and a second calibration material, the second calibration material being for the second material.

12. The method according to claim 11, wherein the second calibration material includes at least one of a polyoxymethylene material and a polymethylmethacrylate material.

13. A method for obtaining an X-ray Dark-Field image of a subject including a first material and a second material, the first and second material having different beam hardening properties, the method comprising:
- acquiring X-ray imaging data of the subject;
- obtaining information as to a contribution of the first material to the acquired X-ray imaging data;
- providing a beam hardening map as an input for the beam hardening correction in the X-ray Dark-Field imaging using the acquired X-ray imaging data, wherein the beam hardening map is based on the obtained information;
- calculating an X-ray Dark-Field image from the acquired X-ray imaging data; and
- correcting the calculated Dark-Field image as to the first material using the beam hardening map and correcting the calculated Dark-Field image as to the second material using attenuation information of the acquired X-ray imaging data.

14. A device for receiving X-ray imaging data and obtaining a beam hardening map used in beam hardening correction in X-ray Dark-Field imaging of a subject including a first material and a second material, the first and second material having different beam hardening properties, the device comprising:
- at least one processor configured to obtain information as to a contribution of the first material to the X-ray imaging data, and
- to provide a beam hardening map as an input for the beam hardening correction in the X-ray Dark-Field imaging using the acquired X-ray imaging data, wherein the beam hardening map is based on the obtained information.

15. A non-transitory computer-readable medium having one or more executable instructions stored thereon which, when executed by at least one processor, cause the at least one processor to perform a method for obtaining a beam hardening map used in beam hardening correction in X-ray Dark-Field imaging of a subject including at least a first material and a second material, the first and second material having different beam hardening properties, the method comprising:
- acquiring X-ray imaging data of the subject;
- obtaining information as to a contribution of the first material to the acquired X-ray imaging data; and
- providing a beam hardening map as an input for the beam hardening correction in the X-ray Dark-Field imaging using the acquired X-ray imaging data, wherein the beam hardening map is based on the obtained information.

* * * * *